(12) United States Patent
Evans

(10) Patent No.: US 6,444,196 B1
(45) Date of Patent: Sep. 3, 2002

(54) HAIR TREATMENT COMPOSITION AND METHOD

(75) Inventor: Benjamin F. Evans, Clementon, NJ (US)

(73) Assignee: Ethnic Magic, Inc., Deptford, NJ (US)

( * ) Notice: Subject to any disclaimer, the term of this patent is extended or adjusted under 35 U.S.C. 154(b) by 0 days.

(21) Appl. No.: 09/609,299

(22) Filed: Jun. 30, 2000

(51) Int. Cl.⁷ .............................. A61K 7/06; A61K 7/08; A61K 7/075; A61K 7/42

(52) U.S. Cl. .................. 424/70.1; 424/70.31; 424/70.9; 424/59

(58) Field of Search .............................. 424/401, 70.1, 424/70.31, 70.9, 59

(56) References Cited

U.S. PATENT DOCUMENTS

| | | |
|---|---|---|
| 3,912,808 A | 10/1975 | Sokol |
| 4,184,974 A * | 1/1980 | Van Leuven |
| 4,563,347 A | 1/1986 | Starch |
| 4,870,010 A | 9/1989 | Hayes |
| 4,999,195 A | 3/1991 | Hayes |
| 5,034,219 A | 7/1991 | Deshpande et al. |
| 5,326,565 A | 7/1994 | Critchley et al. |
| 5,342,611 A | 8/1994 | Komori et al. |
| 5,378,455 A | 1/1995 | Kealey et al. |
| 5,415,855 A | 5/1995 | Critchley et al. |
| 5,618,523 A | 4/1997 | Zysman et al. |
| 5,639,449 A | 6/1997 | Syed et al. |
| 5,639,459 A | 6/1997 | Bouras |
| 5,641,480 A | 6/1997 | Vermeer |
| 5,709,847 A | 1/1998 | Bissett et al. |
| 5,725,875 A | 3/1998 | Noll et al. |
| 5,817,155 A | 10/1998 | Yasuda et al. |
| 5,888,489 A | 3/1999 | Von Mallek |
| 5,935,560 A | 8/1999 | Seper et al. |
| 5,968,530 A | 10/1999 | Arquette |

OTHER PUBLICATIONS

Flick, Cosmetic & Toiletry Formulations, Second Edition, vol. 1, p 438 (1989).*

CTFA, Cosmetic Ingredient Dictionary 3rd Edition (1973) p 246.*

* cited by examiner

Primary Examiner—Thurman K. Page
Assistant Examiner—Humera N. Sheikh
(74) Attorney, Agent, or Firm—Thomas A. Lennox, Esq.

(57) ABSTRACT

A method of manufacture of a water emulsion and a new use of applying the composition to hair that improves the condition of excessively curly hair that has been subjected to a straightening process, the composition including at least three emollients chosen from the group consisting of mineral oil, isopropyl myristate, propylene glycol, cetyl alcohol, and lanolin, stearic acid, and a nonionic surfactant.

18 Claims, No Drawings

HAIR TREATMENT COMPOSITION AND METHOD

FIELD OF THE INVENTION

This invention is directed to the hair treatment field, more particularly to the treatment of natural excessively tightly curled hair that has been subjected to a change in shape, such as straightening or curling processes.

BACKGROUND OF THE INVENTION

Excessively tightly natural curled hair, such as of persons of certain African or Middle Eastern descent, tends to tangle and is difficult to comb. It is popular for hair styling to straighten the naturally excessively curly hair. Many commercial products and developments have been directed to the straightening or "relaxing" such hair. Typical straightening processes use alkalis, such as sodium hydroxide. All of these straightening products tend to injure the hair to varying degrees, resulting in split ends, weakened tensile strength, and compositionally weakened hair strands. It is reported that the straightening process results in chemical degradation of the cysteine bonds of the hair strands. Commercially available "conditioners" fail to provide a satisfactory solution. Prior art compositions and methods for hair treatment are provided herein below and in the comparison examples provided later in the patent.

U.S. Pat. No. 5,415,855 to Critchley, et al, describes a cosmetic composition for topical application to human skin and hair or nails. A wash list of emollients is provided that includes cetyl alcohol, stearic acid, isopropyl and butyl myristate, lanolin, mineral oil and many others. Triton X-100 is listed as one of the emulsifiers. The examples in this patent disclose emollients used in relatively small quantities.

U.S. Pat. No. 5,378,455 to Kealey, et al, describes cosmetic compositions for topical application to human skin and hair for inhibiting hair growth naming various compounds in multiple long all inclusive lists including small quantities of emollients.

U.S. Pat. No. 4,999,195 to Hayes describes personal care compositions for topical application to human skin and hair containing bioemulsifiers including a shampoo with less than 5% emollient and cleansing cream and lotion compositions with less than 15% emollients. U.S. Pat. No. 4,870,010 to Hayes is a similar disclosure.

U.S. Pat. No. 5,342,611 to Komori, et al describes hair cleansing compositions with a claimed range of 20% to 98% of a liquid oil. Specific shampoo compositions includes 20% jojoba oil and a dandruff remover contains 40% olive oil.

U.S. Pat. No. 5,034,219 to Deshpande, et al describes hair conditioner compositions containing less than 15% emollients.

U.S. Pat. No. 5,725,875 to Noll et al. describes protective skin cream compositions, which contain, among many other possible components, nonoxynol-9, identified as Triton AN-101, and emollients, such as glycerin, sorbitol and propyl glycol.

U.S. Pat. No. 5,817,155 to Yasuda et al. describes an emulsion for reducing dripping during the dying of hair. In the "wash lists" of polar oils included in the oil phase of certain compositions, ester oils are listed including alkyl myristates, such as isopropyl myristate, octyldodecyl myristate and myristyl myristate are listed together with dozens of other compounds, and noting that said oils are not preferred. The oils are found in some examples in five percent quantities.

U.S. Pat. No. 5,888,489 to Von Mallek describes conditioning shampoo compositions, including a wash list of emollients, that includes fatty acid esters, such as isopropyl myristate. A disclosure indicates that an emollient is used in 0.5 to 2.0% by weight quantities.

U.S. Pat. No. 5,968,530 to Arquette describes emollient compositions for skin care, preferably containing jojoba oil, wash listing some eighty possible cosmetic uses including hair preparations, specifically hair conditioner, hair spray, hair straighteners, permanent waves, rinses, and shampoos. Specific examples in the patent did not include any hair preparations.

U.S. Pat. No. 5,935,560 to Seper et al. describes compositions and methods to impart durable conditioning properties to hair, specifically using a thiol-functional silicone. Water soluble conditioning agents are shown in long wash list that includes isopropyl myristate and other emollients.

U.S. Pat. No. 5,641,480 to Vermeer describes compositions with heteroatom containing alkyl aldonamide compounds for hair care, especially conditioners, shampoos, conditioning shampoos, and anti dandruff shampoos. A very long wash list of surfactants including nonionic surfactants lists Triton X-100 as the condensation product of octylphenol with about 9 to 10 moles of ethylene oxide. A wash list of hair conditioning agents includes isopropyl myristate and two of 135 examples include mineral oil. None of the examples contain even two of the three compounds.

U.S. Pat. No. 5,709,847 to Bissett et al. describes sun screen skin care compositions containing a radical scavenging compound and an anti inflammatory agent to protect from sun irradiation. The preparations include a large amount of emollient and a wash list includes alkenyl esters of fatty acids with 10 to 20 carbon atoms, lanolin, and wax esters such as myristyl myristate. A wash list of emulsifiers includes a wash list of nonionic emulsifiers and examples contain glycerin and mineral oil.

U.S. Pat. No. 5,639,459 to Bouras describes hair and scalp conditioner compositions containing an oxalate in a paraffin based ointment.

U.S. Pat. No. 5,618,523 to Zysman et al. describes hair and scalp conditioner compositions containing ceramides with a wash list of adjuvants that includes propylene glycol, mineral oil, lanolin and emulsifiers with the fatty phase of the emulsion being 5 to 60 percent of the total weight.

U.S. Pat. No. 5,639,449 to Syed et al. describes a hair strengthening composition for hair that has been exposed to relaxer, the composition containing a water-dispersible polyquaternary ammonium cationic polymer that is applied after a hair swelling component has been added to the hair. Relaxer compositions examples contain up to 18% mineral oil and 12% petrolatum.

None of the prior art compositions and methods teach the present invention or attain the objects provided herein below

SUMMARY OF INVENTION

It is an object of the present invention to provide a composition and a method of use that substantially reduces the incidence to split ends of excessively curly hair that has been subjected to a straightening process or straight hair that has been to a curling process.

It is a further object of the present invention to provide a composition and a method of use that substantially increases the tensile strength and greatly reduces the breakage of excessively curly hair that has been subjected to a straightening process, both immediately and for extended periods of time after treatment.

It is an additional object of the present invention to provide a composition and a method of use that substantially improves the condition of excessively curly hair that has been subjected to a straightening process without introducing chemicals that cause side effects to the health of the hair and scalp.

It is a further object of the present invention to provide a method of producing and applying a composition that, when applied to excessively curly hair that has been subjected to a straightening process, substantially improves the health of the hair, including increasing the elasticity of the hair shaft and enhancing the color of the hair, both indicating restructuring of the hair shaft.

It is an additional object of the present invention to provide a method of producing and applying a composition that, when applied to excessively curly hair that has been subjected to a straightening process, improves the health of the hairline allowing it a chance to develop and avoid breaking off during subsequent washing with soap and with wash cloths.

It is a further object of the present invention to provide a method of producing a composition that, when applied to excessively curly hair that has been subjected to a straightening process, allows the person to go longer without the need of using conditioners.

It is an additional object of the present invention to provide a method of producing a composition that, when applied to excessively curly hair that has been subjected to a straightening process, substantially improves the state of the hair and scalp without the use of conditioning caps, heat caps, and hair dryers, the method of application being accomplished in a relatively short period of time.

An embodiment of the invention is the use of applying a composition to hair that improves the condition of hair that has been subjected to a change of shape, that is excessively curly hair that has been subjected to a straightening process and straight hair that has been subjected to a curling process. The composition includes about 7 to about 40 percent by weight of at least two, and preferably at least three emollients chosen from the group consisting of mineral oil, an alkyl myristate, an alkylene or polyalkylene glycol, a fatty alkyl alcohol having ten to twenty carbon atoms, and lanolin, about one-half to about 10 per cent of a fatty acid, about 3 to about 10 percent by weight of a nonionic surfactant, at least one additional ingredient chosen from the group consisting of fragrances, stabilizing agents, dyes, antimicrobal agents, antibacterial agents, anti agglomerates, and ultraviolet radiation absorbers, and the balance water.

It is preferred that the about 7 to about 40 percent by weight of an emollient mixture include mineral oil and an alkyl myristate present in weight ratios in the range of 3 to 7 and 7 to 3. It is more preferred that the emollient mixture further include at least one emollient chosen from the group consisting of a water soluble alkylene glycol, a fatty acid and lanolin. It is further preferred that the amount of the emollient be in the range of 12 to 25 weight percent, the amount of the nonionic surfactant be in the range of 4 to 8 weight percent, and the amount of the alkyl alcohol be in the range of 3 to 7 weight percent. It is more preferred that the amount of the emollient be in the range of 18 to 22 weight percent, the nonionic surfactant be in the range of 5 to 7 weight percent, and the amount of the alkyl alcohol be in the range of 4 to 6 weight percent. It is further preferred that at least half the emollient be a mixture of mineral oil and an alkyl myristate. It is more preferred that at least two thirds of the emollient be a mixture of mineral oil and an alkyl myristate.

It is also preferred that the emollient be a mixture of mineral oil, an alkyl myristate, an alkylene glycol, a fatty alkyl alcohol having ten to twenty carbon atoms, and lanolin. It is preferred that the amount of the fatty acid be in the range of about one-half to about five percent, and more preferably in the range of about one to about two percent. It is further preferred that the alkyl myristate be isopropyl myristate, the fatty alkyl alcohol having ten to twenty carbon atoms be cetyl alcohol, the fatty acid be stearic acid, and the alkylene glycol be propylene glycol.

A preferred embodiment is a composition that includes an emulsion of about 5 to about 10 percent by weight of mineral oil, about 5 to about 10 percent by weight of isopropyl myristate, about 1 to about 5 percent by weight of propylene glycol, about 1 to about 4 percent by weight of stearic acid, about 5 to about 10 percent by weight of cetyl alcohol, about 3 to about 10 percent by weight of a nonionic surfactant, and the balance water; wherein applying said composition to hair improves the condition of hair that has been subjected to a change of shape.

Another embodiment of the invention is the use of applying the above compositions, wherein applying said composition to hair improves the condition of hair that has been subjected to a change of shape, preferably the condition of excessively curly hair that has been subjected to a straightening process.

Yet another embodiment of the invention is a method of conditioning hair that includes providing a person whose hair has been subjected to a change of shape, providing any of the above compositions, applying the composition to the person's hair, allowing the composition to remain on the hair an effective period of time, and rinsing the composition from the hair with water.

Yet another embodiment of the invention is a method of preparing a composition that when applied to hair improves the condition of hair that has been subjected to a change of shape. The method of conditioning a person's hair includes providing a person whose hair that has been subjected to a change of shape and providing a composition that includes about 7 to about 40 percent by weight of at least two and preferably at least three emollients chosen from the group consisting of mineral oil, an alkyl myristate, an alkylene glycol, a fatty alkyl alcohol having ten to twenty carbon atoms, and lanolin, about one-half to about five percent of a fatty acid, about 3 to about 10 percent by weight of a nonionic surfactant, at least one additional ingredient in an effective quantity chosen from the group consisting of fragrances, stabilizing agents, dyes, antimicrobal agents, antibacterial agents, anti agglomerates, and ultraviolet radiation absorbers, and the balance water. The method further includes applying the composition to the person's hair, allowing the composition to remain on the hair an effective period of time, and rinsing the composition from the hair with water.

Yet another embodiment of the invention is a method of preparing a composition that when applied to hair improves the condition of hair that has been subjected to a change of shape. The method includes mixing together about 7 to about 40 parts by weight of at least two and preferaby three emollients chosen from the group consisting of mineral oil, an alkyl myristate, a fatty alkyl alcohol having ten to twenty carbon atoms, and lanolin, and about one-half to about 10 parts of a fatty acid, to form a first mixture and heating the first mixture to a melt condition. The method further includes mixing together up to about 5 parts by weight of a water soluble alkylene or polyalkylene glycol, about 50 to 90 parts by weight water, about 3 to about 10 parts by weight of a nonionic surfactant, and at least one additional ingredient in an effective amount chosen from the group consisting of fragrances, stabilizing agents, dyes, antimicrobal agents, antibacterial agents, anti agglomerates, and ultraviolet radiation absorbers, to form a second mixture. The method further includes heating the second mixture to a temperature approaching the temperature of the first mixture, slowly adding the first mixture to the second mixture while mixing, and allowing the resultant mixture to cool to room temperature while mixing.

Yet another embodiment of the invention is a composition comprising an emulsion of about 5 to about 10 percent by weight of mineral oil, about 5 to about 10 percent by weight of isopropyl myristate, about 1 to about 5 percent by weight of propylene glycol, about 1 to about 4 percent by weight of stearic acid, about 5 to about 10 percent by weight of cetyl alcohol, about 3 to about 10 percent by weight of a nonionic surfactant, and the balance water; wherein applying said composition to hair improves the condition of hair that has been subjected to an alkali treatment.

DESCRIPTION OF PREFERRED EMBODIMENTS

A unique nature of this invention is that the ingredients contained in this invention work together in a manner that allows the strength of the hair to be regained after its shape has been changed as a result of treatment with alkali. More specifically, this invention allows the emollients and fatty acids to be delivered to the hair and results in arresting the process of excessive breakage of the disulfide bonds in the hair keratin proteins. The proposed mechanism, based on the scientific literature is as follows: The non-ionic surfactant, such as Triton X-100, gently opens the keratin strands to allow the emollients and the fatty acid to penetrate into the protein structure. Once in, the fatty acid neutralizes the excess alkali resulting in the formation of fatty acid soap, and the emollients provide the moisture needed for the disulfide bonds and electrostatic interactions to reestablish themselves. Neutralization of the excess alkali is an essential step in preventing excessive breakage of the disulfide bonds, and allows the reformation of these bonds, thereby allowing the hair to retain its natural strength. The lack of strong electrolytes in the system allows the electrostatic interactions among the amino acid residues in the hair keratin to operate and help maintain the hair strength while the disulfide bonds are being renewed (Crewther, W. G. and Dowling, L. M., *Proc. Internat. Wool Textile Res. Conf. Paris* (CIRTEL), 1965, 2, 393.). Furthermore, the low ionic strength of this invention prevents the formation of too many "lanthionine" bonds in the hair protein, which is detrimental to the hair and renders the hair untreatable with thioglycollic acid preparations. In summary, this invention has the unique combination of ingredients to reestablish the hair strength in its new shape, thereby preventing the common problems of weakened hair after an alkali treatment.

Important ingredients of the present invention fall into the general category of emollients that include, but are not limited to hydrocarbon oils and waxes, such as mineral oil, petrolatum, and the like, vegetable and animal oils and fats, such as olive oil, palm oil, castor oil, corn oil, soybean oil, and the like, and lanolin and its derivatives, such as lanolin, lanolin oil, lanolin wax, lanolin alcohols, and the like. Other emollients include esters of fatty acids having 10 to 20 carbon atoms, such as including myristic, stearic, isostearic, palmitic, and the like, such as methyl myristate, propyl myristate, butyl myristate, propyl stearate, propyl isostearate, propyl palmitate, and the like. Other emollients include fatty acids having 10 to 20 carbon atoms, including stearic, myristic, lauric, isostearic, palmitic, and the like. Emollients also include fatty alcohols having ten to twenty carbon atoms, such as cetyl, myristyl, lauryl, isostearyl, stearyl and the like. Although some are water soluble, polyhydric alcohols and polyether derivatives are included as emollients, including glycols, glycerol, sorbitol, polyalkylene glycols and the like, such as propylene glycol, dipropylene glycol, polyethylene glycol 200–500, and the like. The water soluble examples are preferred.

Another important ingredient is an emulsifier/surfactant and nonionic surfactants are preferred which are broadly described as polyoxyalkylene oxide condensation products of hydrophobic alkyl, alkene, or alkyl aromatic functional groups having a free reactive hydrogen available for condensation with hydrophilic alkylene oxide, polyethylene oxide, propylene oxide, butylene oxide, polyethylene oxide or polyethylene glycol to form nonionic surfactants. Particularly effective are the condensation products of octylphenol with about 7 to about 13 moles of ethylene oxide, sold by the Rohm & Haas Company under their trademark TRITON® 100 series products.

Other ingredients are included in the compositions for purposes and in quantities well known in the art to be effective, including but not limited to fragrances, stabilizing agents, dyes, antimicrobal agents, antibacterial agents, anti agglomerates, ultraviolet radiation absorbers, and the like.

To illustrate the present invention the following examples are prepared.

EXAMPLE 1

An emulsion is prepared as follows:

| The following compounds are added to a 500 ml beaker: | |
|---|---|
| mineral oil | 70 grams |
| isopropyl myristate | 55 grams |
| lanolin | 5 grams |
| cetyl alcohol | 50 grams |
| stearic acid | 15 grams |
| propyl paraben | 1 gram |

The beaker is heated until the mixture melts at about 65° C. and the compounds are stirred maintaining this Mixture A in that condition.

| The following compounds are added to a 2000 ml beaker: | |
|---|---|
| distilled water | 725 grams |
| Triton X-100 | 60 grams |
| propylene glycol | 15 grams |

The 2000 ml beaker is heated to about 65° C. while the mixture is stirred. Mixture A is slowly poured into the mixture in the 2000 ml beaker while the Sample 1 mix is gently stirred. The heat source is removed and the Sample 1 mix is allowed to cool to room temperature, while the stirring is continued. The emulsion is reasonably stable and pourable. Sample 1 is placed in polyethylene plastic squeeze bottles for use and testing under Example 2 herein below.

EXAMPLE 2

To illustrate the utility and performance of the emulsion of Sample 1, it is compared in performance to commercially available hair conditioners.

Sample 2-FIN is a commercially available hair conditioner described as extra moisturizing conditioner for dry hair providing softness and body to overstyled hair. This product is further described as a dual action formula that softens and protects dry, damaged hair and replenishes and restores moisture to the hair. The ingredients of Sample 2-FIN are water, cetyl alcohol, stearyl alcohol, cyclomethicone, stearyl octyldimonium methosulfate, glycerin, sodium PCA hydrolyzed soil protein, hydroxyethylcellulose, citric acid, stearamidopropyl dimethylamine, behenamidopropyl ethyldimonium ethosulfate, amodimethicone, and tallowtrimonium chloride, nonoxynol-10, fragrance, methylchloroisothiazolinone, methylisothiazolinone, DMDM hydantoin, and disodium EDTA.

Sample 2-BAN is a commercially available hair conditioner described as leaving the hair naturally bright, soft and shiny while removing the yellowing from gray hair. This product is also reported to be approved for use after sodium hydroxide or no-lye relaxers. The ingredients of Sample 2-BAN are water, ceteareth-20, cetearyl alcohol, cetyl alcohol, hydrogen peroxide, pentasodium pentetate, polyquaternium-22, stearalkonium chloride and water.

Sample 2-WAV is a commercially available hair conditioner described as providing moisture and conditioning to dry, brittle hair aiding in revitalizing damaged, limp waves and curls and restoring tensile strength. It is reported that the hair responds with body and improved manageability. The ingredients of Sample 2-WAV are cetearyl alcohol and polysorbate 60, cetyl alcohol, collagen amino acids, acetamide MEA, silk amino acids, propylene glycol, deionized water, fragrance, glyceryl stearate SE, hydrolyzed animal protein, lecithin, methylparaben, propylparaben, and stearalkonium chloride.

To compare the effectiveness of the samples after the hair of a person's head has been straightened using a commercially available composition containing sodium hydroxide using standard commercially recommended procedures, each sample is applied to a quarter section of the person's head. Before testing the hair is thoroughly washed and rinsed. In the first quarter section of the head Sample 2-FIN is applied liberally to the hair and allowed to remain on the hair for three minutes. In the first section the hair is separated into bundles of about ten strands of hair using a comb. A single bundle is gripped below the middle of the length between the thumb and forefinger and the bundle is pulled slowly allowing the bundle to slide between the thumb and finger as continuous tensile force is applied. As the grip slides along the bundle toward the end breakage and the integrity of the hair strands are observed until only a single hair strand is gripped and pulled until it breaks or it is clear that the hair strand will be pulled out before it breaks. For Sample 2-FIN, as the grip slides toward the end of the bundle, the shorter strands slip out and as the number of strands reaches a few in number, some of the strands break and the last strand breaks, with the broken ends of the hairs remaining in the grip and the still attached base of the broken strands curling up. Almost all of the last strands gripped break. This same test is repeated two more times with bundles located in a different area of the quarter section with essentially identical results.

The above testing procedure is repeated with Samples 2-BAN and 2-WAV on different quarter sections of the person's head with very similar results. Again with each of these two Samples, there is substantial breaking of the strands including the last strand in each of the three tests.

Finally, the above testing procedure is repeated with Sample 1 on the final quarter section of the person's head. However, the results are dramatically different as the three bundles of strands are pulled toward the ends. In each case there is no breakage as the grip approaches the end of the bundle and in two out of three cases even the last strand do not break as they slip from the grip.

The entire head of hair is then washed and rinsed; and the above gripping and pulling test is repeated on bundles in each of the four quarter sections of the head. There is substantial breakage of the strands in the three sections treated with Samples 2-FIN, 2-BAN and 2-WAV, and almost no breakage in the section treated with Sample 1. This procedure is to demonstrate the effectiveness of the invention, and it should be noted that it is not necessary to wash or even rinse the hair treated according to this invention.

The entire head of hair is then dried; and the above gripping and pulling test is repeated on bundles in each of the four quarter sections of the head. There is substantial breakage of the strands in the three sections treated with Samples 2-FIN, 2-BAN and 2-WAV, and almost no breakage in the section treated with Sample 1.

The entire procedure is repeated on three different persons with the location of the samples on the heads moved clockwise a quarter turn on each person, so that each sample is tested on all different quarter sections of the head. On all the persons tested, there is substantial breakage of the strands in the three sections treated with Samples 2-FIN, 2-BAN and 2-WAV, and almost no breakage in the section treated with Sample 1.

The entire procedure is repeated on heads that have hair subjected to extreme curling procedures using an alkali treatment. Again the section treated with Sample 1 is superior to the sections treated with Samples 2-FIN, 2-BAN and 2-WAV.

EXAMPLE 3

To further illustrate the present invention in the following procedures samples are prepared as listed on Table 1 using the method described in Example 1. These samples are tested using the procedures described in Example 2.

TABLE 1

Compositions (Weight percent) of Samples Prepared According To The Procedures Of Example 1

| Sample # | 3-1 | 3-2 | 3-3 | 3-4 | 3-5 | 3-6 | 3-7 | 3-8 | 3-9 | 3-10 | 3-11 | 3-12 | 3-13 | 3-14 |
|---|---|---|---|---|---|---|---|---|---|---|---|---|---|---|
| Mineral Oil Myristates | 2 | 7 | 8 | 11 | 8 | — | — | 8 | 8 | 8 | 8 | 8 | 8 | — |
| isopropyl | 1 | 4 | 6 | 8 | 8 | 8 | — | 5 | — | 6 | 6 | 6 | 6 | — |
| butyl | — | — | — | — | — | — | — | — | 6 | — | — | — | — | — |

TABLE 1-continued

Compositions (Weight percent) of Samples Prepared According To The Procedures Of Example 1

| Sample # | 3-1 | 3-2 | 3-3 | 3-4 | 3-5 | 3-6 | 3-7 | 3-8 | 3-9 | 3-10 | 3-11 | 3-12 | 3-13 | 3-14 |
|---|---|---|---|---|---|---|---|---|---|---|---|---|---|---|
| Alcohols | | | | | | | | | | | | | | |
| stearyl | — | — | — | — | — | — | — | — | — | 5 | — | — | — | — |
| cetyl | 1 | 3 | 5 | 6 | 5 | 5 | 5 | — | 5 | — | 5 | 5 | 5 | 5 |
| Surfactants | | | | | | | | | | | | | | |
| Triton X-100 | 1 | 3 | 6 | 8 | 8 | 8 | 8 | 8 | 6 | 6 | — | 6 | 6 | 8 |
| Triton X-101 | — | — | — | — | — | — | — | — | — | — | 6 | — | — | — |
| Glycols | | | | | | | | | | | | | | |
| propylene | 0.5 | 1 | 2 | 2.5 | 1 | 1 | 1 | 1 | 2 | 2 | 2 | — | 2 | 1 |
| dipropylene | — | — | — | — | — | — | — | — | — | — | — | 2 | — | — |
| Lanolin | — | 1 | 1 | 1.5 | — | — | 8 | — | — | — | — | — | — | — |
| Olive Oil | — | — | — | — | — | — | — | — | — | — | — | — | — | 8 |
| Fatty Acids | | | | | | | | | | | | | | |
| stearic | 0.5 | 2 | 2 | 3 | — | 8 | 8 | 8 | 3 | 3 | 3 | 3 | — | 8 |
| lauric | — | — | — | — | — | — | — | — | — | — | — | — | 3 | — |
| Water | 94 | 80 | 70 | 60 | 70 | 70 | 70 | 70 | 70 | 70 | 70 | 70 | 70 | 70 |

Samples 3-1 through 3-14 are prepared using the procedures of Example 1 with adjustments in temperature and time as required. Each sample is tested according to the procedures of Example 2 on at least one head of hair. Some of the samples 3-1 through 3-14 perform almost as well as Sample 1 and all perform at least slightly better than the three commercial products tested in Example 2, with the exception of sample 3-5, which performs equally well.

While this invention has been described with reference to specific embodiments disclosed herein, it is not confined to the details set forth and the patent is intended to include modifications and changes which may come within and extend from the following claims.

I claim:

1. A composition comprising an emulsion of:
   (a) about 5 to about 10 percent by weight of mineral oil,
   (b) about 5 to about 10 percent by weight of isopropyl myristate,
   (c) about 1 to about 5 percent by weight of propylene glycol,
   (d) about 1 to about 4 percent by weight of stearic acid,
   (e) about 5 to about 10 percent by weight of cetyl alcohol,
   (f) about 3 to about 10 percent by weight of a nonionic surfactant, and
   (g) the balance water; wherein applying said composition to hair improves the condition of hair that has been subjected to an alkali treatment.

2. A method of treating hair that has been subjected to an alkali treatment, the method comprising:
   (A) providing a composition comprising:
      (a) about 7 to about 40 percent by weight of at least three emollients chosen from the group consisting of mineral oil, an alkyl myristate, an alkylene or polyalkylene glycol, a fatty alkyl alcohol having ten to twenty carbon atoms, and lanolin,
      (b) about one-half to about 10 percent by weight of a fatty acid,
      (c) about 3 to about 10 percent by weight of a nonionic surfactant,
      (d) at least one additional ingredient chosen from the group consisting of fragrances, stabilizing agents, dyes, antimicrobal agents, antibacterial agents, antiagglomerates, and ultraviolet radiation absorbers, and
      (e) the balance water, and
   (B) applying the composition to the hair.

3. The method of claim 2, wherein the amount of the emollient is in the range of 12 to 25 weight percent, the amount of the fatty acid is in the range of 0.5 to 5 weight percent and the amount of the nonionic surfactant is in the range of 4 to 8 weight percent.

4. The method of claim 2, wherein the amount of the emollient is in the range of 18 to 22 weight percent, the amount of the fatty acid is in the range of 1 to 2 weight percent, and the amount of the nonionic surfactant is in the range of 5 to 7 weight percent.

5. The method of claim 4, wherein at least half the emollient is a mixture of mineral oil and an alkyl myristate.

6. The method of claim 5, wherein at least two thirds of the emollient is a mixture of mineral oil and an alkyl myristate.

7. The method of claim 2, wherein the emollient is a mixture of mineral oil, an alkyl myristate, an alkylene glycol, a fatty alkyl alcohol having ten to twenty carbon atoms, and lanolin.

8. The method of claim 7, wherein the alkyl myristate is isopropyl myristate, the alcohol is cetyl alcohol and the alkylene glycol is propylene glycol.

9. A composition comprising:
   (a) about 7 to about 40 percent by weight of at least three emollients chosen from the group consisting of mineral oil, an alkyl myristate, an alkylene glycol, a fatty alkyl alcohol having ten to twenty carbon atoms, and lanolin,
   (b) about one-half to about 10 percent by weight of a fatty acid,
   (c) about 3 to about 10 percent by weight of a nonionic surfactant,
   (d) at least one additional ingredient chosen from the group consisting of fragrances, stabilizing agents, dyes, antimicrobal agents, antibacterial agents, antiagglomerates, and ultraviolet radiation absorbers, and
   (e) the balance water; wherein applying said composition to hair improves the condition of hair that has been subjected to an alkali treatment.

10. The composition of claim 9, wherein the amount of the emollient is in the range of 12 to 25 weight percents, the amount of the fatty acid is in the range of 0.5 to 5 weight percent, and the amount of the nonionic surfactant is in the range of 4 to 8 weight percent.

11. The composition of claim 9, wherein the amount of the emollient is in the range of 18 to 22 weight percent, the amount of the fatty acid is in the range of 1 to 2 weight percent, and the nonionic surfactant is in the range of 5 to 7 weight percent.

12. The composition of claim 11, wherein the emollient is a mixture of mineral oil, an alkyl myristate, an alkylene or polyalkylene glycol, a fatty acid, a fatty alkyl alcohol having ten to twenty carbon atoms, and lanolin.

13. The composition of claim 12, wherein the alkyl myristate is isopropyl myristate, the fatty alkyl alcohol is cetyl alcohol and the alkylene glycol is propylene glycol.

14. A method of conditioning hair comprising:
  (i) providing a person whose hair that has been subjected to an alkali treatment,
  (ii) providing a composition comprising:
    (a) about 7 to about 40 percent by weight of at least two emollients chosen from the group consisting of mineral oil, an alkyl myristate, an alkylene glycol, a fatty alkyl alcohol having ten to twenty carbon atoms, and lanolin,
    (b) about one-half to about 10 percent by weight of a fatty acid,
    (c) about 3 to about 10 percent by weight of a nonionic surfactant,
    (d) at least one additional ingredient chosen from the group consisting of fragrances, stabilizing agents, dyes, antimicrobal agents, antibacterial agents, antiagglomerates, and ultraviolet radiation absorbers, and
    (e) the balance water,
  (iii) applying the composition to the person's hair,
  (iv) allowing the composition to remain on the hair an effective period of time, and
  (v) rinsing the composition from the hair with water.

15. The method of claim 14, wherein the amount of the emollient is in the range of 12 to 25 weight percent, the amount of the fatty acid is in the range of 0.5 to 5 weight percent, and the amount of the nonionic surfactant is in the range of 4 to 8 weight percent.

16. The method of claim 14, wherein the amount of the emollient is in the range of 18 to 22 weight percent, the amount of the fatty acid is in the range of 1 to 2 weight percent, and the nonionic surfactant is in the range of 5 to 7 weight percent.

17. The method of claim 16, wherein the emollient is a mixture of mineral oil, an alkyl myristate, an alkylene glycol, a fatty alkyl alcohol having ten to twenty carbon atoms, and lanolin.

18. The method of claim 17, wherein the alkyl myristate is isopropyl myristate, the alcohol is cetyl alcohol, the fatty acid is stearic acids and the alkylene glycol is propylene glycol.

* * * * *